United States Patent
Wright et al.

(10) Patent No.: US 6,395,907 B1
(45) Date of Patent: May 28, 2002

(54) PREPARATION OF POLYAROMATIC-ETHYNYL THERMAL SETTING AGENTS

(75) Inventors: Michel E. Wright, Mechanicsville; Derek Schorzman, Richmond, both of VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 09/714,791

(22) Filed: Nov. 17, 2000

Related U.S. Application Data

(60) Provisional application No. 60/166,212, filed on Nov. 18, 1999.

(51) Int. Cl.$^7$ .................. C07D 209/38; C07D 307/89; C08G 69/26; C08G 14/00
(52) U.S. Cl. .............. 548/513; 549/247; 528/353; 528/125; 528/170
(58) Field of Search .......... 548/513; 549/247; 528/353, 125, 170

(56) References Cited

U.S. PATENT DOCUMENTS

| | | | | |
|---|---|---|---|---|
| 5,412,066 A | * | 5/1995 | Hergenrother et al. ...... | 528/353 |
| 5,599,993 A | * | 2/1997 | Hergenrother et al. ...... | 564/328 |
| 5,681,967 A | * | 10/1997 | Hergenrother et al. ...... | 549/243 |
| 5,760,168 A | * | 6/1998 | Hergenrother et al. ...... | 528/353 |
| 6,084,106 A | * | 7/2000 | Crook et al. ................ | 548/406 |
| 6,136,949 A | * | 10/2000 | Earls et al. ................. | 528/353 |

* cited by examiner

*Primary Examiner*—Deborah C. Lambkin
(74) *Attorney, Agent, or Firm*—Whitham, Curtis & Christofferson, P.C.

(57) ABSTRACT

The present invention is directed to new polycyclicaromatic-ethynyl terminated materials that possesses excellent mechanical and chemical properties for high-performance composite application that can be cured at lower temperatures than phenyl-ethynyl terminated imide materials.

33 Claims, 11 Drawing Sheets

PREPARATION OF POLYAROMATIC-ETHYNYL THERMAL SETTING AGENTS

This Application is based on and claims priority to U.S. Provisional Application No. 60/166,212, filed Nov. 18, 1999, herein incorporated by reference in its entirety.

BACKGROUND OF THE INVENTION

Phenyl-ethynyl terminated imide oligomers can be thermally cured to afford a final resin that possesses excellent mechanical and chemical properties pivotal to high-performance composite applications. The cured phenyl-ethynyl terminated resins possess improved thermo-oxidative stability and processability over thermally cured acetylene-terminated imide oligomer resins. Typical curing temperatures for the neat oligomer are generally near 350° C. and the chemical reaction(s) leading to the final resin appears to be multifaceted.

The entire cure process appears to follow a complicated rate law. Some of the most recent studies have suggested that first-order (pseudo) kinetics are followed for the initial 90 percent of the reaction for both an oligomeric material and a bis-phenylethynyl model compound. Other mechanistic studies have demonstrated the complexity of the curing process. In each study performed, there is reasonably good agreement between the kinetic data observed for oligomeric material and their model compound analogs. This point appears to validate the use and study of small molecules to probe both the mechanism and products for at least a majority of the curing reaction(s).

There is a need for a resin that possesses excellent mechanical and chemical properties for high-performance composite application that can be cured at lower temperatures than the phenyl-ethynyl terminated imide materials.

SUMMARY OF THE INVENTION

It is an object of the present invention to provide compounds that can be cured at lower temperatures than the phenyl-ethynyl terminated imide materials.

Another object of the present invention is to incorporate polycyclic aromatic rings in aryl-ethynyl end-capping groups. This substitution provides the necessary thermal stability and provides a significant change in stereoelectronics.

It is an object of the present invention to prepare new aryl-ethynyl model compounds and end-capped oligomeric materials.

Further, another object of the present invention is to develop pre-polymers which can be cured at lower temperatures yet produce a final material that possesses the excellent chemical, thermal, and mechanical properties associated with NASA's thermally cured PETI-5 (Phenyl-Ethynyl Terminated Imide) oligomer.

To these ends, the present invention is directed to the synthesis, thermal curing, and kinetic analysis of a naphthyl-ethynyl imide-model compounds, which cure at a significantly faster rate than the phenyl-ethynyl analog. The present invention is also directed to naphthyl-ethynyl anhydride compounds, anthracenyl-ethynyl imide model compounds, and anthracenyl-ethynyl anhydride compounds.

The present invention includes a compound having the formula:

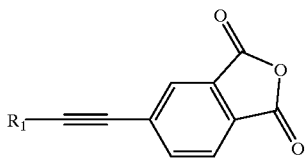

wherein $R_1$ is a polycyclicaromatic moiety. $R_1$ may be 9-anthracenyl, 1-napthyl, or 2-napthyl.

The present invention also includes a method for preparing a compound comprising the steps of reacting an anhydride having the formula:

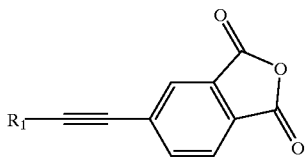

with a reactive compound where the reactive compound is reactive to the anhydride and where $R_1$ is a polycyclicaromatic moiety. $R_1$ may be selected from the group consisting of 1-napthyl, 2-napthyl, and 9-anthracenyl. The reactive compound may be selected from the group consisting of amines, diamines, triamines, compounds having more than three amino functional groups, phenoxy benzyl diamines, diamines containing aryl substituents, sulfonyl containing compounds, halide containing compounds, ester containing compounds, amide containing compounds, and combinations thereof. The reactive compound may preferably be a thermally stable aromatic bis(amine). Further, the reactive compound may be selected from the group consisting of

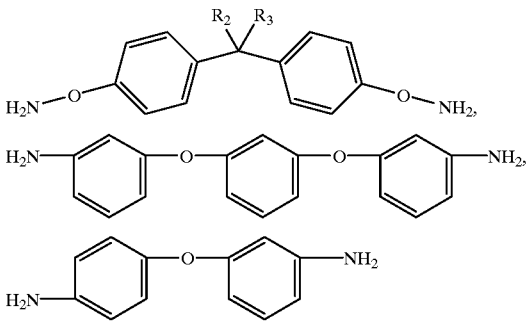

and combinations thereof, where $R_2$ and $R_3$ are alkyl moieties. $R_2$ and $R_3$ may be methyl or other short chain alkyls, $C_1$–$C_6$, and may be the same or different.

The present invention further includes a compound having the formula:

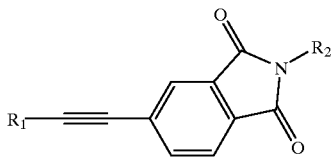

wherein $R_1$ is a polycyclicaromatic moiety. $R_1$ may be selected from the group consisting of 1-napthyl, 2-napthyl, and 9-anthracenyl. $R_2$ may be an alkyl moiety selected from the group consisting of hydrogen, phenyl, and $C_1$ to $C_{50}$ alkyl. Further, $R_2$ may be a reactive functional group selected from the group consisting of amino, sulfonyl, halide, ester, and amide functional groups.

Still further, the invention includes a compound having one of the following formulas:

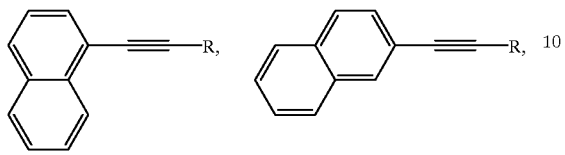

and

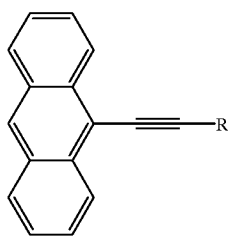

where R is selected from the group consisting of polymers, oligimers, and reactive moieties. R may be a polymer selected from the group consisting of polyimides, polysulfones, polyaromatics, and polyolefins. Further, R may be a reactive moiety selected from the group consisting of phthalimide and phthalic anhydride.

Further, the invention includes a method for making an polycyclicaromatic-ethynyl capped compound comprising reacting the a polycyclicaromatic-ethynyl compound having one of the following formulas:

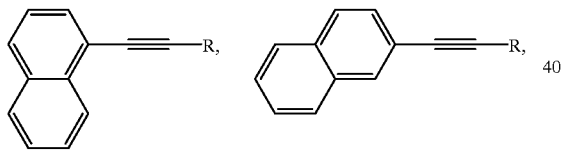

and

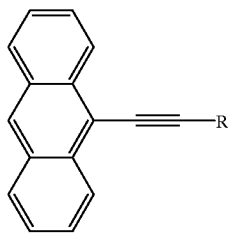

with a reactive compound where R is an anhydride moiety to produce a polycyclicaromatic-ethynyl capped compound. The reactive compound may be selected from the group consisting of amines, diamines, triamines, compounds having more than three amino functional groups, phenoxy benzyl diamines, diamines containing aryl substituents, sulfonyl containing compounds, halide containing compounds, ester containing compounds, amide containing compounds, and combinations thereof. Further, the reactive compound may be a thermally stable aromatic bis(amine).

Still further, the reactive compound may be selected from the group consisting of

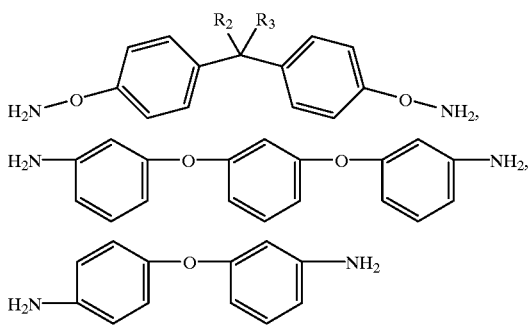

and combination thereof, where $R_2$ and $R_3$ are alkyl moieties. $R_2$ and $R_3$ may be methyl moieties or other short alkyls, $C_1$–$C_6$, and may be the same or different. The anhydride portion of the polycylicaromatic ethynyl compound may include, but is not limited to 3,3',4,4'-biphenyltetracarboxylic dianhydride, 4,4'-oxydiphthalic anhydride, and combinations thereof. In one embodiment, R may be phthalic anhydride.

The present invention also includes a method for making a polymer comprising:

reacting

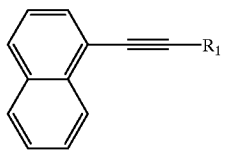

with

X—$R_2$ to produce

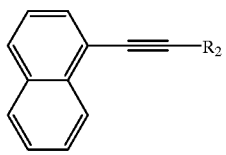

wherein $R_1$ is a metal anion, X is a halogen, and $R_2$ is a polymer.

Still further the invention also includes a method for making a polymer comprising reacting

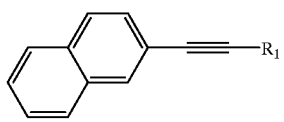

with

X—$R_2$ to produce

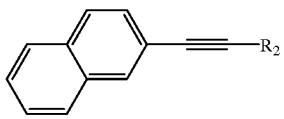

wherein $R_1$ is a metal anion, X is a halogen, and $R_2$ is a polymer.

Still further, the present invention includes a method for making a polymer comprising:

reacting

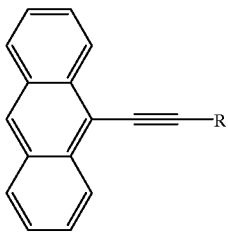

with

to produce

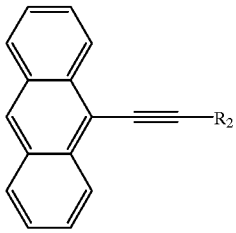

wherein R is a metal anion, X is a halogen, and $R_2$ is a polymer.

In the cases noted above, the polymer R2 can be a wide variety of different materials including, but not limited to, polyimides, polyamides, polyethers, polysulfones, epoxides, polyalkyls such as polyethylenes, and polycycloaromatics including heteroaromatics.

DETAILED DESCRIPTION OF THE INVENTION

Figure 1:
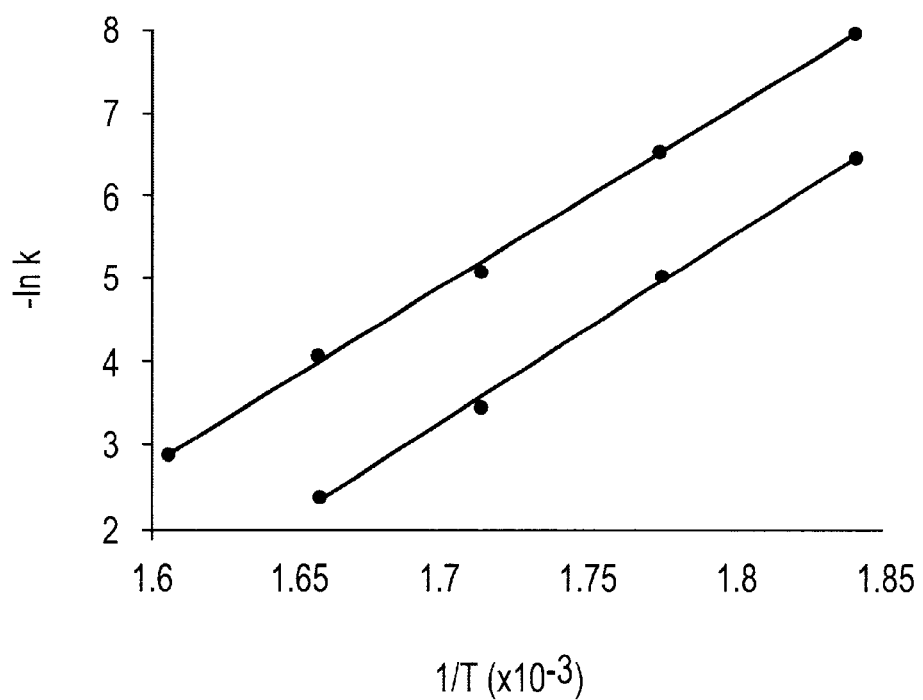
FIG. 1 is an Arrhenius plot of thermal cure of model compounds: ■=naphthyl-ethynyl model, r=0.998; ♦=phenyl-ethynyl model compound, r=0.997.

The present invention is directed to new polycyclicaromatic-ethynyl model compounds and end-capped oligomeric and polymeric materials. The invention includes pre-polymers which can be cured at lower temperatures yet produce a final material that possesses the excellent chemical, thermal, and mechanical properties associated with NASA's thermally cured PETI-5. The present invention includes the synthesis, thermal curing, and kinetic analysis of naphthyl-ethynyl imide-model compounds which cure at a significantly faster rate than the phenyl-ethynyl analog. The present invention also includes naphthyl-ethynyl anhydride compounds, anthracenyl-ethynyl imide model compounds, and anthracenyl-ethynyl anhydride compounds.

The substitution of polycyclic aromatic rings provide the necessary thermal stability and provide a significant change in stereoelectronics (to be discussed further below). Compounds of the present invention include:

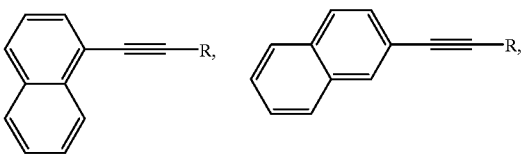

and

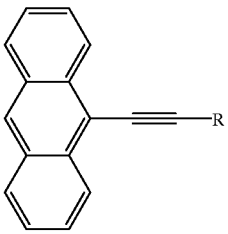

where $R_1$ may be a polymer, oligimer or a reactive moiety. Polymers may be virtually any polymer. Some exemplary polymers include, but are not limited to, polyimides, polysulfones, polyolefins, polyaromatics, and polyamides.

Oligimer are similar to the polymers except the oligimer typically only have a few repeating units and have a lower molecular weight than the polymers. Alternatively, R may be a reactive moiety for placing the compound on the end of a polymer or oligimer. An exemplary reactive moiety for use with an amine containing compound would be an anhydride. Preferably, the reactive moiety is either phthalimide or an anhydride such as 3,3',4,4'-biphenyltetracarboxylic dianhydride or 4,4'-oxydiphthalic anhydride.

The above polycyclicaromatic-ethynyl compounds may be used to cap a polymer or oligimer. In addition the reaction of the polymer or oligimer with the anhydride polycyclicaromatic-ethynyl compound or the reactive functional group on the phthalimide polycyclicaromatic-ethynyl compound, discussed in detail below, R could be a metal anion such as an alkali metal ion. Such a compound would be reacted with a halide containing polymer, X-$R_2$, where $R_2$ is a polymer or oligimer. In this way, the polycyclicaromatic-ethynl end cap would replace the halide to form polycyclicaromatic-ethynyl-$R_2$.

The present invention includes an anhydride having the following formula:

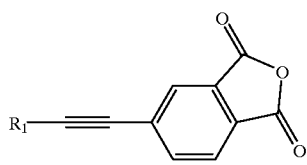

where $R_1$ is a polycyclicaromatic moiety. $R_1$ may include, but is not limited to 9-anthracenyl, 1-napthyl, or 2-napthyl. Further, the polycyclicaromatic-acetylenyl group may be position in any position on the six membered carbon ring. The preferable location for the polycyclicaromatic-acetylenyl group is as illustrated.

The above anhydride may be reacted with a reactive compound to form a polycyclicaromatic capped compound. As used herein, "reactive compound" is a compound that will react with the anhydride and produce a compound having a higher molecular weight than the anhydride. The reactive compound may include, but is not limited to amines, diamines, triamines, compounds having more than three amino functional groups, phenoxy benzyl diamines, diamines containing aryl substituents, sulfonyl containing compounds, halide containing compounds, ester containing compounds, amide containing compounds, and combinations thereof. Further, the reactive compound may be a thermally stable aromatic bis(amine). Preferably, the reactive compound includes, but is not limited to,

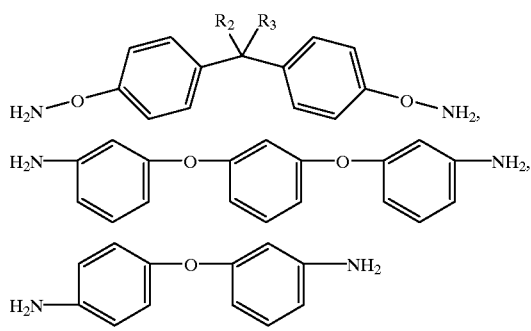

and combinations thereof. $R_2$ and $R_3$ may be hydrogen or an alkyl group. Preferably, $R_2$ and $R_3$ are methyl groups.

Additionally, the invention includes the imide having the general formula:

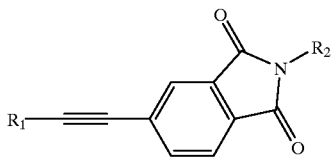

where $R_1$ is a polycyclicaromatic moiety and $R_2$ is an alkyl moiety. This imide compound is useful as a model compound for studying potential properties of the anhydride and is also useful as a compound for placing the polycyclicaromatic end cap on a polymer or oligimer. $R_1$ is a polyaromatic moiety that may include, but is not limited to, 1-napthyl, 2-napthyl, and 9-anthracenyl. $R_2$ may be an alkyl group or a reactive functional group. If $R_2$ is an alkyl, it may include, but is not limited to hydrogen, phenyl, and $C_{1-50}$ alkyl groups. Where $R_2$ is a reactive functional group to place the imide on the end of a polymer or oligimer, the reactive functional group may include, but is not limited to, amino, sulfonyl, halide, ester, and amide functional groups. There may be alkyl portions between the imide portion and the reactive functional group. The reactive functional group would be selected depending on the polymer or oligimer to be used. The pairing of reactive functional group to the polymer or oligimer is selected according to general chemical principles known to one skilled in the art.

The naphthyl-ethynyl model (1) was prepared in high yield using standard ethynylation techniques. Compound 1 was isolated in 55% overall yield as a yellow crystalline solid.

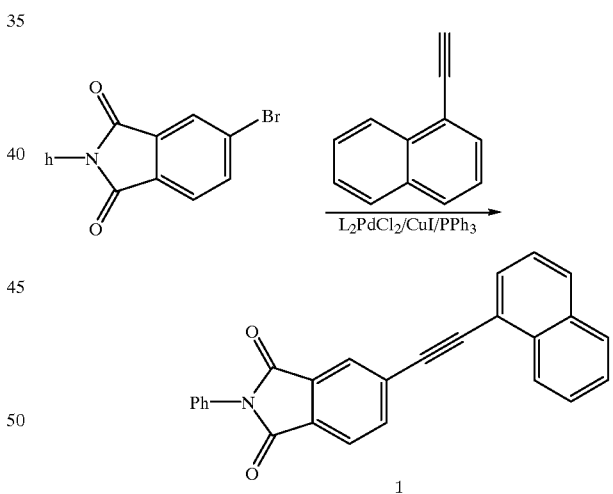

Thermal curing of 1 was carried out in sealed pyrex vessels under a nitrogen atmosphere. A set of 8 samples were placed in a calibrated aluminum heating block and at selected reaction times, a sample was removed and then analyzed by proton-NMR spectroscopy. The entire sample was dissolved in $CDCl_3$ that contained an integration standard of 1,2-dichloroethane. The concentrations were determined directly by integration of the NMR signals for the phthalimide singlet at δ8.20 ppm to the dichloroethane singlet at δ3.73 ppm. It is important to note that all reaction samples were completely soluble in the NMR solvent (both products and reactants) for all data points. In addition, we observed an induction period for each sample that we attribute to the time needed for the sample to equilibrate to the heating block temperature. Applying first order data analysis (i.e. $\ln(C/C_0)$ versus time) we obtained uniformly good line fits and used the observed rate constants (k) in Arrhenius plots to determine the apparent energy of activation ($E_a$). In order to strike a better comparison we also performed a kinetic analysis on the phenyl-ethynyl imide model compound: N-phenyl-[4-(phenylethynyl) phthalimide] (2) (FIG. 1).

The $E_a$ values found for 1 and phenyl-ethynyl model compounds are 45±1.7 kcal/mol and 42.5±1.0 kcal/mol, respectively. The activation energy we measure for the phenyl-ethynyl compound is somewhat higher than that determined previously (36.5 kcal/mol). The value of 42.5 kcal/mol for 2 is similar to a related model compound, 3,4'-bis[4-(phenylethynyl)phthalimido]diphenyl ether, which also follows first order kinetics ($E_a$=40.7±2.7 kcal/mol). The fact that the energy of activation is higher for the naphthyl-ethynyl compound yet the reaction rate is faster at normal curing temperatures is intriguing and useful. Hence, we can obtain similar cure rates for the naphthyl-ethynyl analog at a temperature ~30° C. below that needed for the phenyl-ethynyl system.

Figure 2:
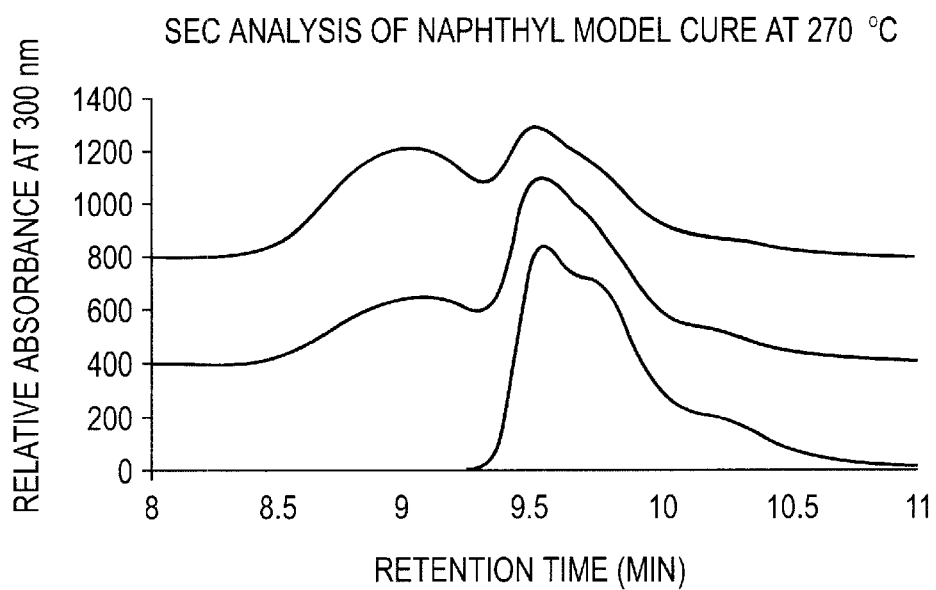
FIG. 2 shows size exclusion chromatography ("SEC") analysis of the naphthyl-ethynyl model compound at: top trace, t=360 min. ($C/C_0$=0.56); t=1.80 min. ($C/C_0$=0.80); bottom, t=0 min. ($C/C_0$=1.00).

Size exclusion chromatography (SEC) was used to analyze the curing model reactions to better understand the products and help in confirming that the curing reaction of the naphthyl and phenyl systems are similar (FIG. 2). SEC analyses of reaction samples were performed by dilution in THF (2 mg/mL) and then injection on to Hewlett Packard 1100 HPLC (column: PL 300×7.5 mm, 5 $\mu$ particle size). Molecular weights were calculated relative to polystyrene standards. In each kinetic run studied, low molecular weight material formed (~1000) with no indication of the formation of oligomeric or polymeric products. These data support the premise that the naphthyl-system is undergoing similar curing chemistry to the phenyl-ethynyl model compound. Thermal gravimetric analysis under a nitrogen atmosphere also showed the two systems to possess similar thermal stability (>300° C.).

The significant increase in the rate of curing for the naphthyl-ethynyl system must be due to a difference in the Arrhenius constant. Hence, there are reaction parameters such as stereoelectronic factors and collisional parameters that enable the naphthyl-ethynyl system to produce more successful results (i.e. curing of the ethynyl-group) for a given amount of applied external energy. A brief examination of molecular orbital calculations suggest indeed there are significant differences between the highest occupied molecular orbitals (HOMO) of 1 and 2. Notably, the HOMO orbital shows a great deal of "movement" from the alkyne in 2 to the naphthyl-ring (carbon-4 in particular) in 1.

N-phenyl-(1-naphthylethynyl)phthalimide (1) was prepared in 55% overall yield. Neat samples of 1 were subjected to thermal curing at temperatures ranging from 270 to 330° C. The extent of reaction was determined by NMR spectroscopic analysis of the cured samples. In all cases, both reactant and products were readily and completely soluble in chloroform. An Arrhenius plot of the kinetic data yielded an apparent energy of activation for the curing reaction of 45±1.7 kcal/mol. The phenyl-ethynyl analog was also studied and found to have a smaller energy of activation (42.5±1.0 kcal/mol); however, the phenyl-ethynyl analog had a much slower rate of reaction at the curing temperatures used in this study. Thus, the new naphthyl-ethynyl imide is found to cure at a significantly faster rate for typical curing temperatures.

Various aspects of the present invention are illustrated in the following examples. The examples are provided for illustration purposes and should not be construed as limiting the scope of the present invention.

EXAMPLE 1

Model Compounds and Imide Oligomer Syntheses. Model compounds N-phenyl-4-(1-naphthylethynyl) phthalimide (1), N-phenyl-4-phenylethynylphthalimide (2), and N-phenyl-4-(2-naphthylethynyl)phthalimide (3) shown in Chart 1 were prepared in good yield using standard ethynylation techniques. Compound 3 exhibited a unique lack of solubility in chloroform. This combined with spectral peak overlaps questioned whether the correct compound was obtained. Thus, 3 was synthesized using two independent synthetic pathways (Scheme 1). In each case, the same identical product was produced and has been unambiguously assigned the structure of 3 based on spectroscopic and analytical data.

Chart I

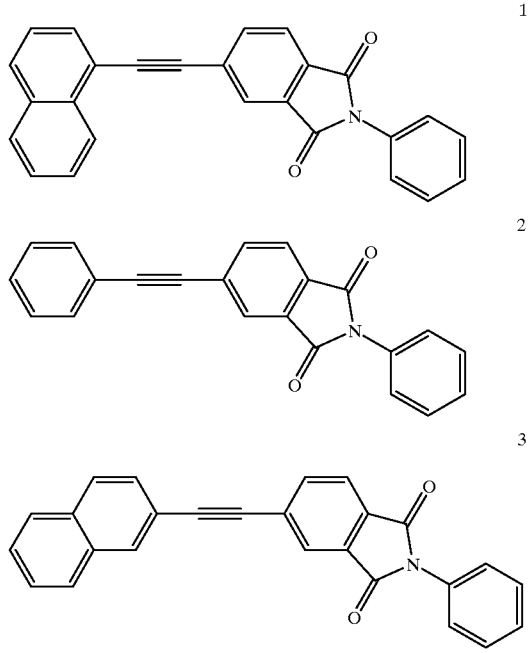

Scheme I

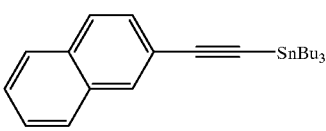

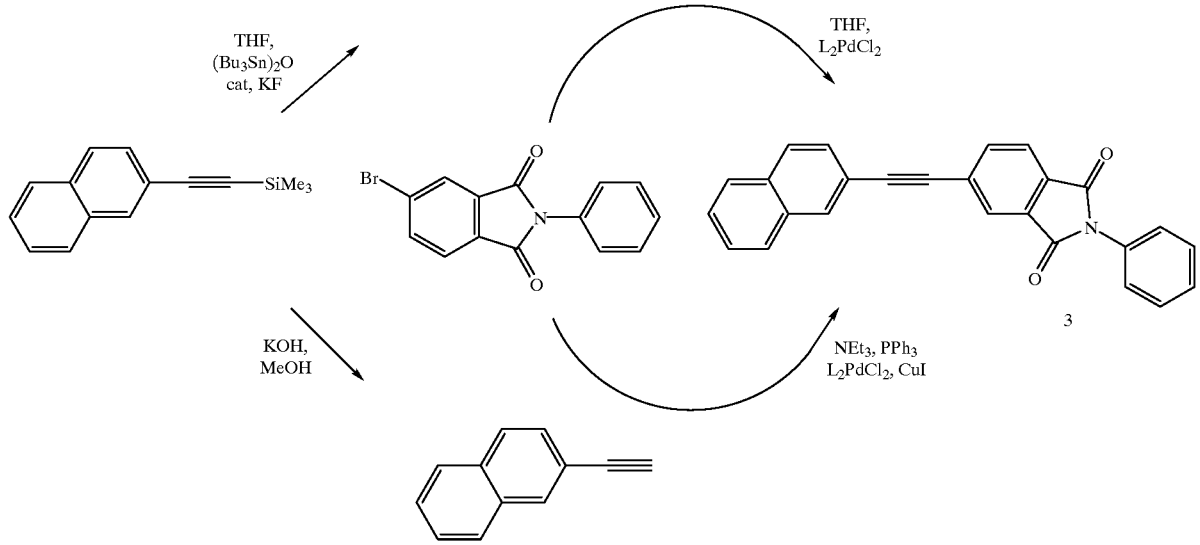

The PETI-5 (Phenyl-Ethynyl Terminated Imide oligomer) and NETI-5 (Naphthyl-Ethynyl Terminated Imide oligomer) oligomers were prepared to a theoretical molecular weight of 5000 g/mol using the previously reported technique.[7] The NETI-5 oligomer incorporated our new end-capping reagent, 4-(1-naphthylethynyl)phthalic anhydride (4-NEPA). As expected the naphthyl-moiety showed no discernable effect on the reactivity of the anhydride group and the oligomeric materials were generated in very good yield. NETI-5 displayed similar physical properties (e.g. $T_g$) and solubility in common organic solvents.

reveals bond distances of 1.41(1), 1.21(1), and 1.42(1) Å. The presence of three molecules in the asymmetric unit of the 1-naphthyl-ethynyl structure, 1, offers an unusual opportunity to compare three examples of the same structure under the same conditions. The structure consists of three rigid ring systems linked through two points of flexibility or twist. The phenyl rings bonded to the N of the phthalimide have similar torsion angles of 124, 126, and 127° in the three molecules respectively, typical for systems with no ortho substituents on the phenyls.[20-22] The ethynyl triple bond represents the second source of twist in the molecules. Two

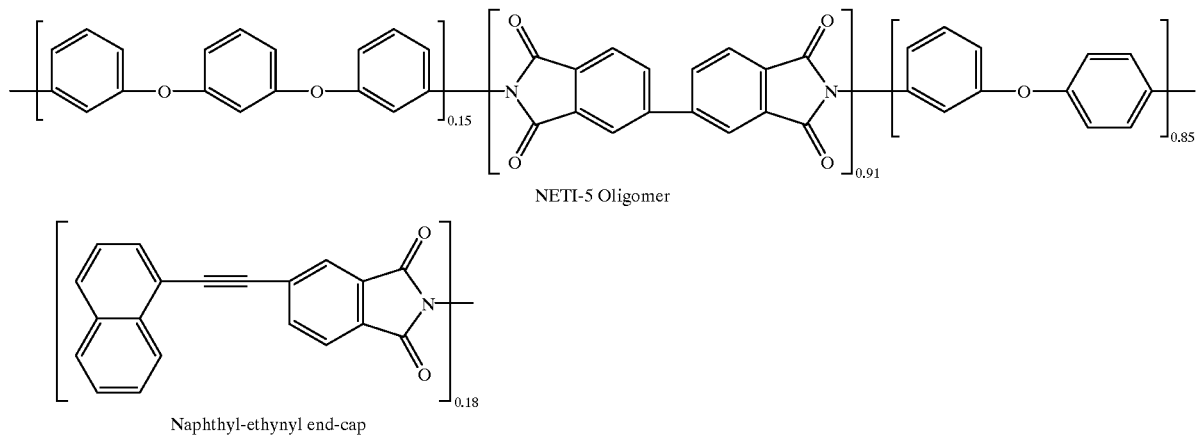

To better understand the reactivity differences we find in the aryl-ethynyl moieties a series of single-crystal molecular structure determinations on the model compounds have been carried out. Single-crystals of 1 and 2 were obtained by diffusing pentane into a chloroform solution containing the appropriate compound. Drawings for the molecular structures are displayed in FIGS. 3 and 4.

Figure 3:
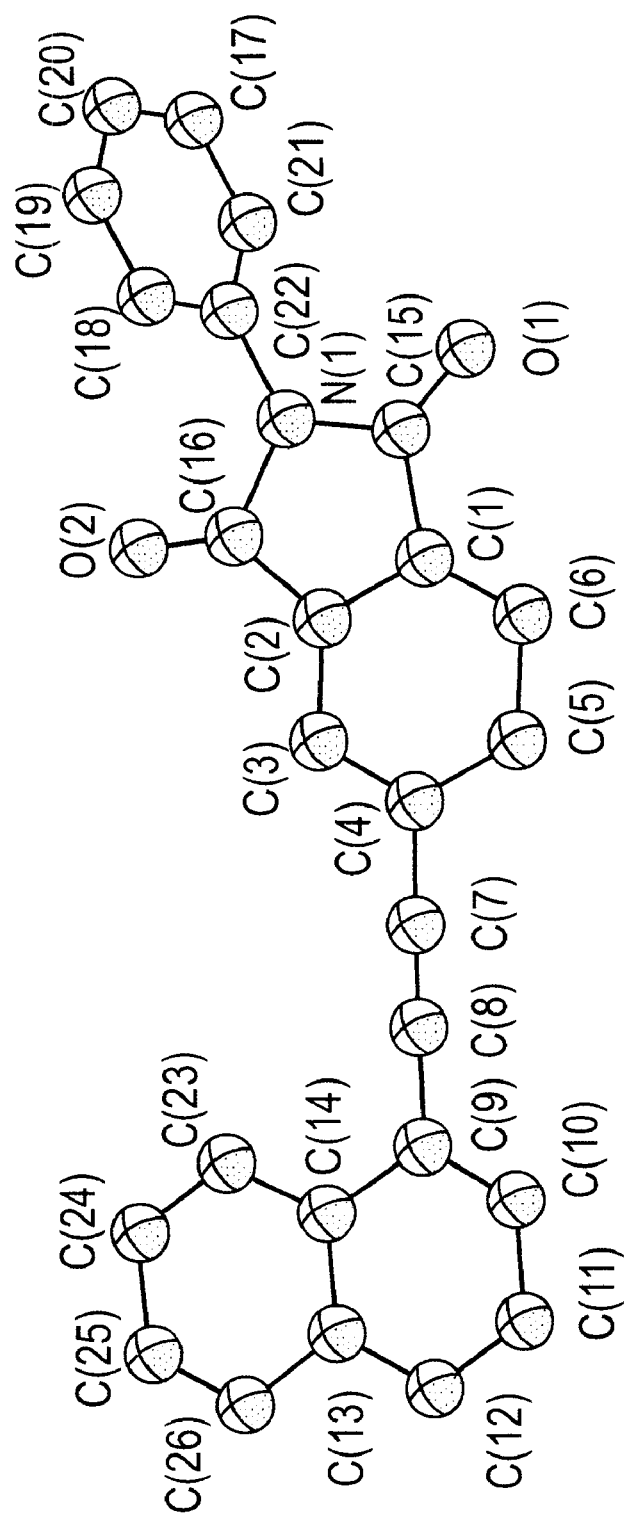
FIG. 3 is an ORTEP view of N-phenyl-4-(1-naphthylethynyl)phthalimide, molecule 1a, showing the 50% probability thermal ellipsoids. The hydrogen atoms are omitted for clarity.
Figure 4:
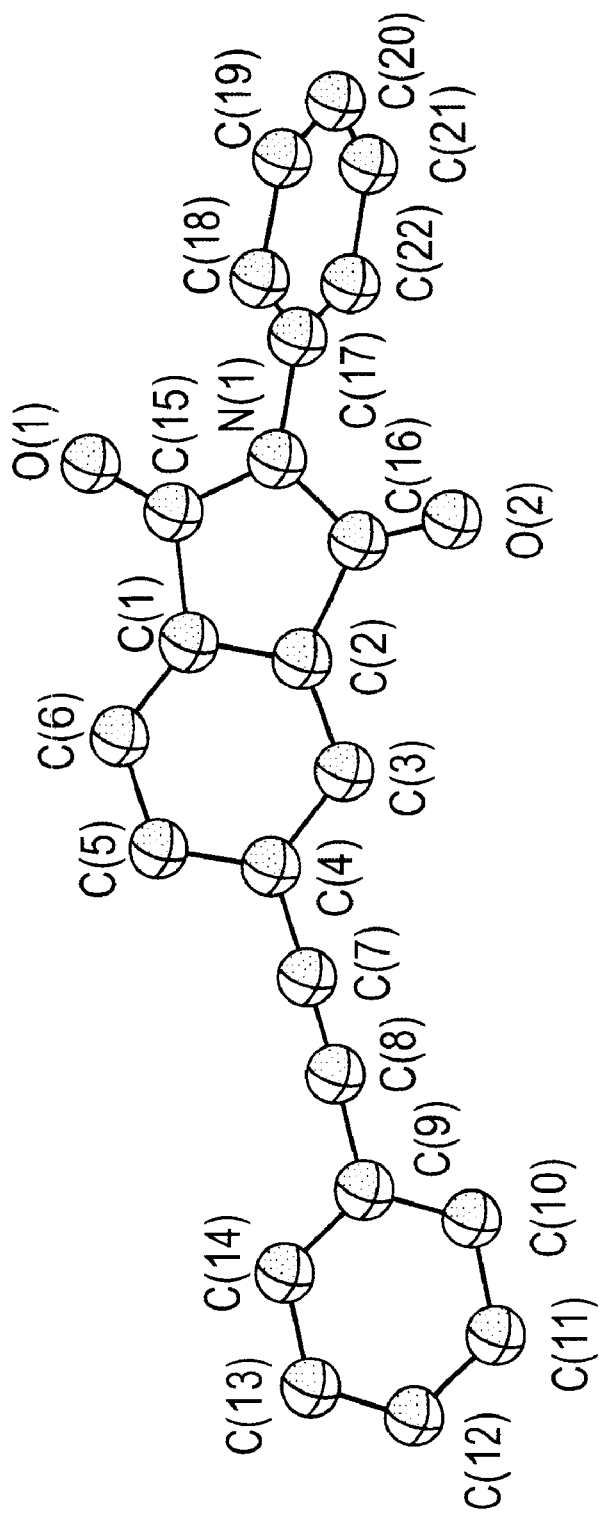
FIG. 4 is an ORTEP view of N-phenyl-4-phenylethynylphthalimide (2) showing the 50% probability thermal ellipsoids. The hydrogen atoms are omitted for clarity.

Overall we find that the bond distances for structures of 1 and 2 show no significant differences in key functional group areas. For example, the alkyne-linkage in 1 we observe bond distances for C(4)–C(7), C(7)–C(8), and C(8)–C(9) of 1.46 (1), 1.19 (1), and 1.41(1) Å, respectively. A comparison to 2 of the molecules, molecule 1a and molecule 1b, as shown in FIG. 3, have a torsion angle of 160 and 162° respectively between the phthalimide-ring system and the naphthyl ring system. In molecule 1c, the angle is only 8° for the same measurement resulting in an orientation in which the bulk of the naphthyl-ring is on the same side as C(5) and C(6) of the phthalimide moiety in comparison to molecules 1a and 1b in which the bulk of the naphthyl-ring is on the opposite side from atoms C(5) and C(6).

Figure 5:
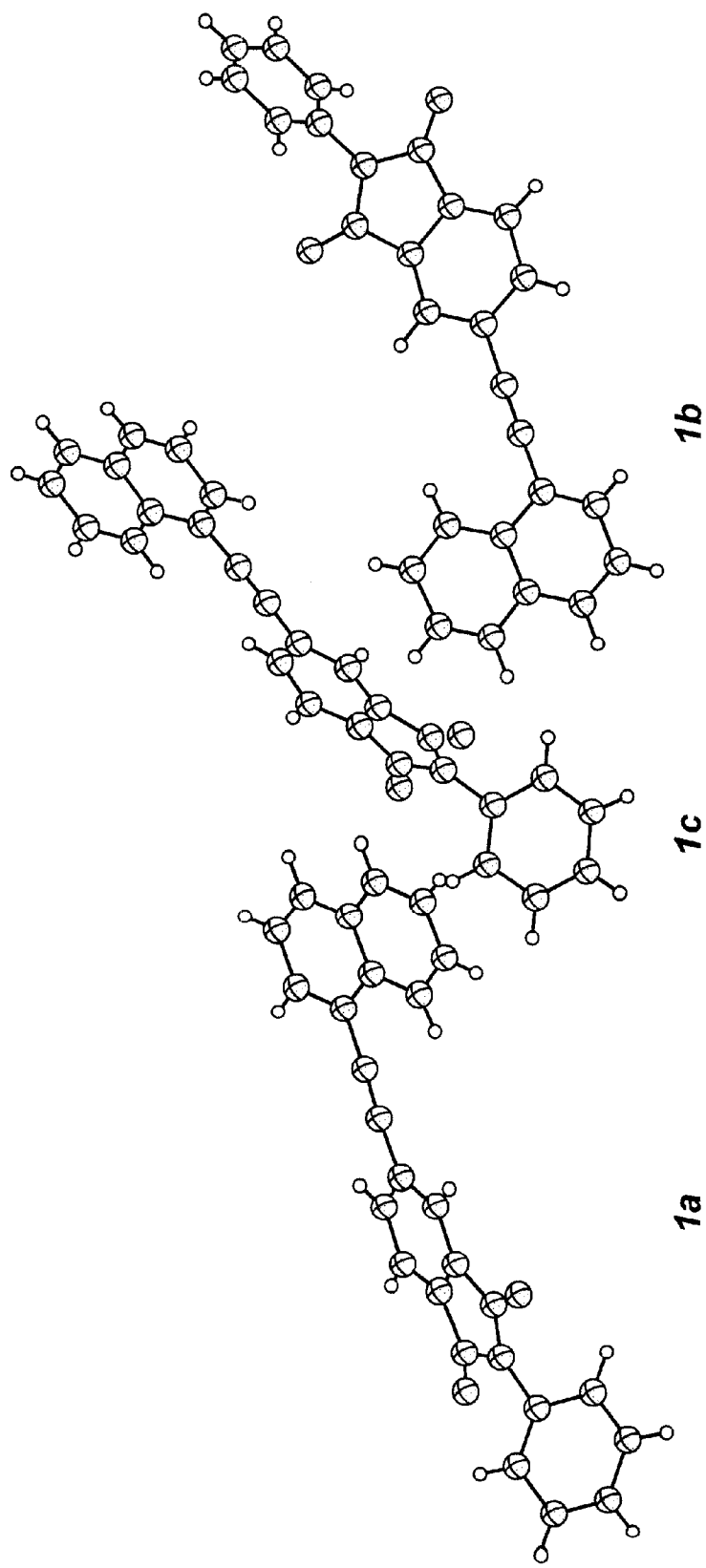
FIG. 5 is an ORTEP view of the asymmetric unit for compound 1 displaying molecule 1c in the center between molecules 1a and 1b.
Figure 6:
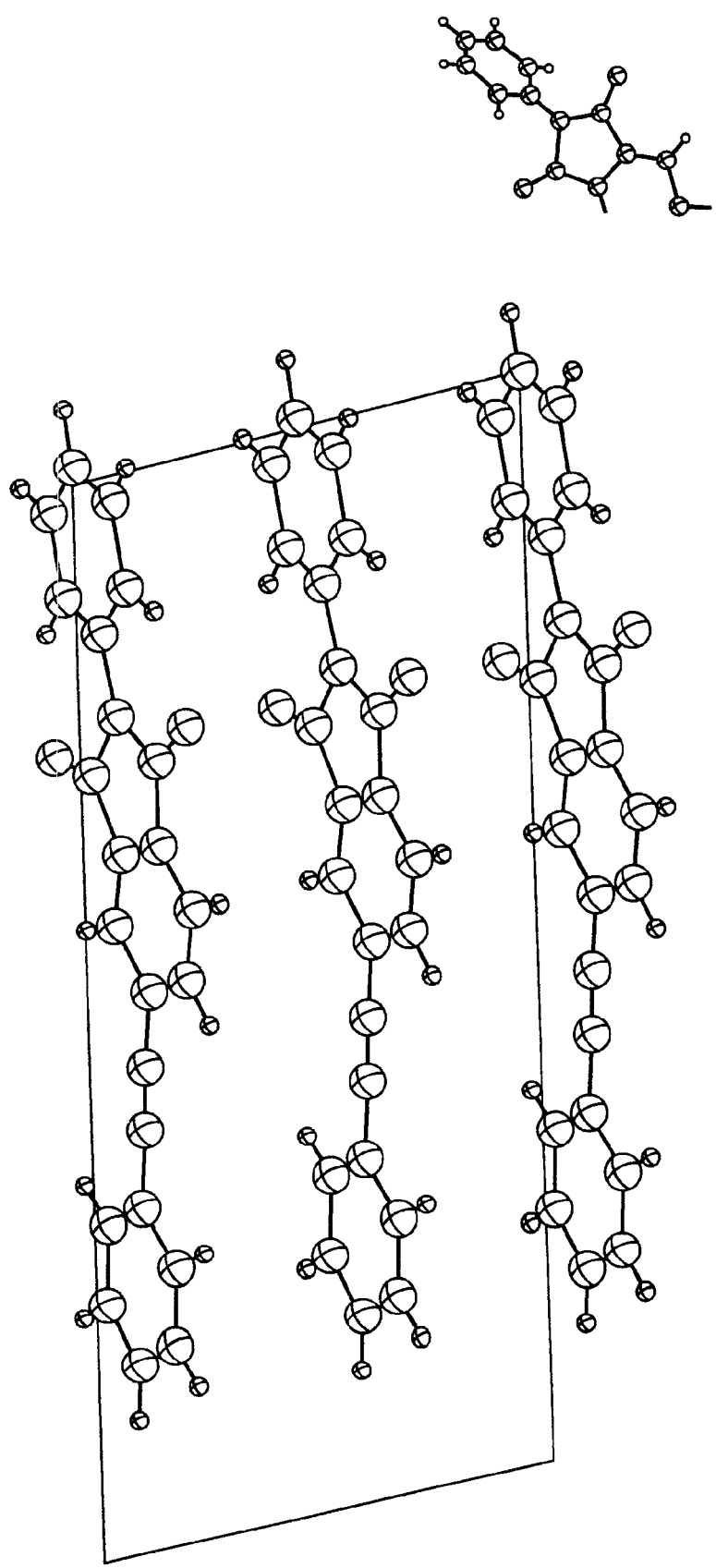
FIG. 6 shows a unit cell packing diagram of 2 looking down the b axis. The rear layer, which has the identical orientation to the front layer shown, has been omitted for clarity.

We find the molecular packing for the two molecular structures shows a very intriguing difference as shown in FIGS. 5 and 6. The asymmetric unit as shown in FIG. 5 demonstrates the similarity between the outer molecules 1a and 1b, but the lack of an inversion center is clearly displayed by the presence of molecule 1c in the center, which confirms the choice of the a centric space group. The phenyl-ethynyl structure, 2, crystallizes with a single molecule in the asymmetric unit. Examination of the packing diagram in FIG. 6 shows that the molecules pack with "heads and tails" aligned and not alternating, again removing the inversion center and verifying the low symmetry space group. This packing mode contrasts with asymmetric unit of 1 in which the molecules instead orient head to tail, and as a result do not display the complementary conformations shown in FIG. 6. The extremely efficient packing of 2 ($d_{calcd}$=1.343 g cm$^{-3}$)is demonstrated by close intermolecular contacts under 3.0 Å for O(1)–C(16), O(1)–O(2), O(1)–N(1), O(2)–C(15), and O(2)–N(1), although the lack of ring stacking is indicated by only two unimportant C-C contacts under 3.6 Å, 3.52(1) Å for C(3)–C(6), and 3.56(2) Å for C(11)–C(14). Overall compound 1 packs more densely ($d_{calcd}$=1.352 g cm$^{-3}$) even though the closest intermolecular contacts are approximately 3.2 Å each from O(2)–C(16), O(102)–C(116), and O(201)–C(110). At this time it is unclear how these differences in packing directly relate to the difference in reactivity (i.e. rate of curing) for compounds 1 and 2. However, the crystal structures do show that when the molecules approach in the condensed state there are distinct differences found in the intermolecular arrangements and forces.

Acquiring Kinetic Data for the Curing Reactions. For each of the model systems studied an array of sealed glass tubes each containing a known amount of model compound was heated. At specified reaction times a single glass tube was removed from the heating block and cooled to ambient temperature. The remaining samples in the heating block were unaffected by each sample removal.

The excellent CDCl$_3$ solubility of 1 and 2, both before and after thermal cure, permitted us to employ proton NMR spectroscopic analysis as to measure the kinetics of curing. More specifically, the aromatic protons of 1 and 2 are found to move upfield and collapse into a single broad peak (approximately δ7–8 ppm) as the thermal curing process moves along. Each sample was completely dissolved in CDCl$_3$ that contained an integration standard of 1,2-dichloroethane. The concentration of unreacted model compound was determined directly by integration of the proton NMR signals for the phthalimide singlet (1, δ8.20; 2, δ8.08) to the 1,2-dichloroethane singlet (δ3.73 ppm). In addition, we observed an induction period (Time α Temperature$^{-1}$) for each sample that we attribute to equilibration to the heating block temperature. Applying first-order data analysis (ie. ln(C/C$_0$) vs. time) we obtained uniformly good line fits and used the observed rate constants (k) in Arrhenius plots to determine the energy of activation (E$_a$) and Eyring plots (i.e. ln[(C/C$_0$)/T] vs. 1/T) to determine thermodynamic parameters. To strike a better comparison we also performed $^1$H NMR kinetic analysis on the phenyl-ethynyl model compound (2). Several samples were analyzed by Size Exclusion Chromatography (SEC) by dilution in THF (2 mg/mL) and then injection onto a Hewlett-Packard 1100 HPLC (column: PL 300×7.5 mm, 5 μm particle size). Molecular weights are calculated relative to polystyrene standards.

Poor solubility of 3 in CDCl$_3$ precluded us from performing a $^1$H NMR spectro-kinetic analysis. As before, compounds 2 and 3 were thermally cured but now each sample was mixed with KBr and formed into a pellet and then analyzed on a Nicolet Magna FT-IR 760 spectrometer. Concentrations for the reactant model compound were determined by integration of the alkyne $v_{C \equiv C}$ stretch (2, 2216 cm$^{-1}$; 3, 2209 cm$^{-1}$) to the integration of the $v_{C-H}$ peaks (2, 3068 cm$^{-1}$ to 3018 cm$^{-1}$; 3, 3058 cm$^{-1}$ to 3032 cm$^{-1}$). The $v_{C-H}$ peaks offered an ideal internal integration standard due to the occurrence in a region free from other peaks and with an intensity similar to that of the alkyne $v_{C \equiv C}$ peak. In addition, no gaseous by-products were detected during the thermal cure of the model compounds, as has been previously reported for PETI-5 and other model compounds. The induction period consisted of an increase in alkyne stretch intensity relative to the internal standard peak(s) to approximately 130% of the initial value. We attribute this increase in intensity to a reorganization of the molecules within the solid state. Applying first-order analysis for data following the induction period, we obtained uniformly good line fits and used these rate constants in Arrhenius and Eyring plots. The analyses were also performed on the phenyl-ethynyl model compound (2) as our reference point. Tables I and II below show the Arrhenius and Eyring analysis of the kinetic data for the model compounds and oligomers.

TABLE I

Arrhenius analysis of kinetic data for model compounds and oligomers.

| Analysis Method | $^1$H NMR | $^1$H NMR | FTIR | FTIR | DSC | DSC |
|---|---|---|---|---|---|---|
| Sample | 1 | 2 | 2 | 3 | PETI-5 | NETI-5 |
| R$^2$ | 0.9969 | 0.9986 | 0.9989 | 0.9998 | 0.9997 | 0.9968 |
| Slope* | −22639 | −21411 | −15172 | −23877 | −18810 | −19556 |
|  | (897) | (464) | (494) | (349) | (347) | (1111) |
| Intercept* | 35.23 | 31.49 | 20.75 | 36.75 | 25.09 | 27.46 |
|  | (157) | (80) | (85) | (60) | (56) | (178) |
| E$_a$ (kcal/mol)* | 44.99 | 42.55 | 30.15 | 47.45 | 37.38 | 38.86 |
|  | (178) | (92) | (98) | (69) | (69) | (221) |
| A (min$^{-1}$) | 10$^{15}$ | 10$^{13}$ | 10$^9$ | 10$^{15}$ | 10$^{10}$ | 10$^{11}$ |

*Number in parentheses represent standard deviation error for the last significant digits

TABLE II

Eyring analysis of kinetic data for model compounds and oligomers.

| Analysis Method | $^1$H NMR | $^1$H NMR | FTIR | FTIR | DSC | DSC |
|---|---|---|---|---|---|---|
| Sample | 1 | 2 | 2 | 3 | PETI-5 | NETI-5 |
| R$^2$ | 0.9967 | 0.9985 | 0.9988 | 0.9998 | 0.9996 | 0.9996 |
| Slope* | −22067 | −20830 | −14590 | −23295 | −18187 | −18933 |
|  | (899) | (466) | (500) | (355) | (341) | (1116) |
| Intercept* | 27.88 | 24.13 | 13.38 | 29.38 | 17.65 | 20.03 |
|  | (157) | (80) | (86) | (61) | (55) | (179) |
| ΔH$_{act}$* (kcal/mol) | 43.85 | 41.39 | 28.99 | 46.29 | 36.14 | 37.62 |
|  | (179) | (93) | (99) | (71) | (68) | (222) |
| ΔS$_{act}$* (cal/K*mol) | 8.1 | 0.6 | −20.7 | 11.1 | −12.2 | −7.5 |
|  | (31) | (16) | (17) | (12) | (11) | (36) |

*Numbers in parentheses represent standard deviation error for the last significant digits The kinetic analysis of the oligomeric systems of PETI-5 and NETI-5 were also carried out as above, however due to a lack of solubility and dilution of the ethynyl-functional group the progress of the reaction was followed by DSC. Hence, at various time intervals a sample was removed from the heating block and then analyzed on a Perkin-Elmer DSC-7 (under dinitrogen, flow rate of 40 cm$^3$/min, ramp rate of 10° C./min). The extent of cure was calculated using the DiBenedetto equation, modified for highly crosslinked networks:

$$(T_g - T_{gu})/(T_{gc} - T_{gu}) = \lambda x/(1-(1-\lambda)x)$$

where $T_g$ represents the glass transition temperature of the model compound after thermal curing at each temperature, $T_{gu}$ is the glass transition temperature of the uncured model compound, $T_{gc}$ is the glass transition temperature of fully cured model compound, $\lambda$ is the ratio of the isobaric heat capacity of fully cured model compound to that of uncured model compound, and x is the reaction extent (ie. $C/C_0=1-x$). DSC analysis of uncured NETI-5 revealed a melting peak at 264° C. in the first scan and a $T_{gu}$ of 230° C. in the second scan. Similarly, uncured PETI-5 consisted of a melting peak at 263° C. in the first scan and a $T_{gu}$ of 237° C. in the second scan. The $\lambda$ and $T_{gc}$ values determined by Fang et al.[1b] corresponded well with both NETI-5 and PETI-5 and were used in our calculations ($\lambda=0.69$, $T_{gc}=69.9°$ C.). It has been previously reported that properties of the imide oligomers and the cured resins are nearly identical regardless of the end-capping compound. Applying first-order data analysis we obtained uniformly good line fits and used the observed rate constants in Arrhenius and Eyring plots.

Figure 7:
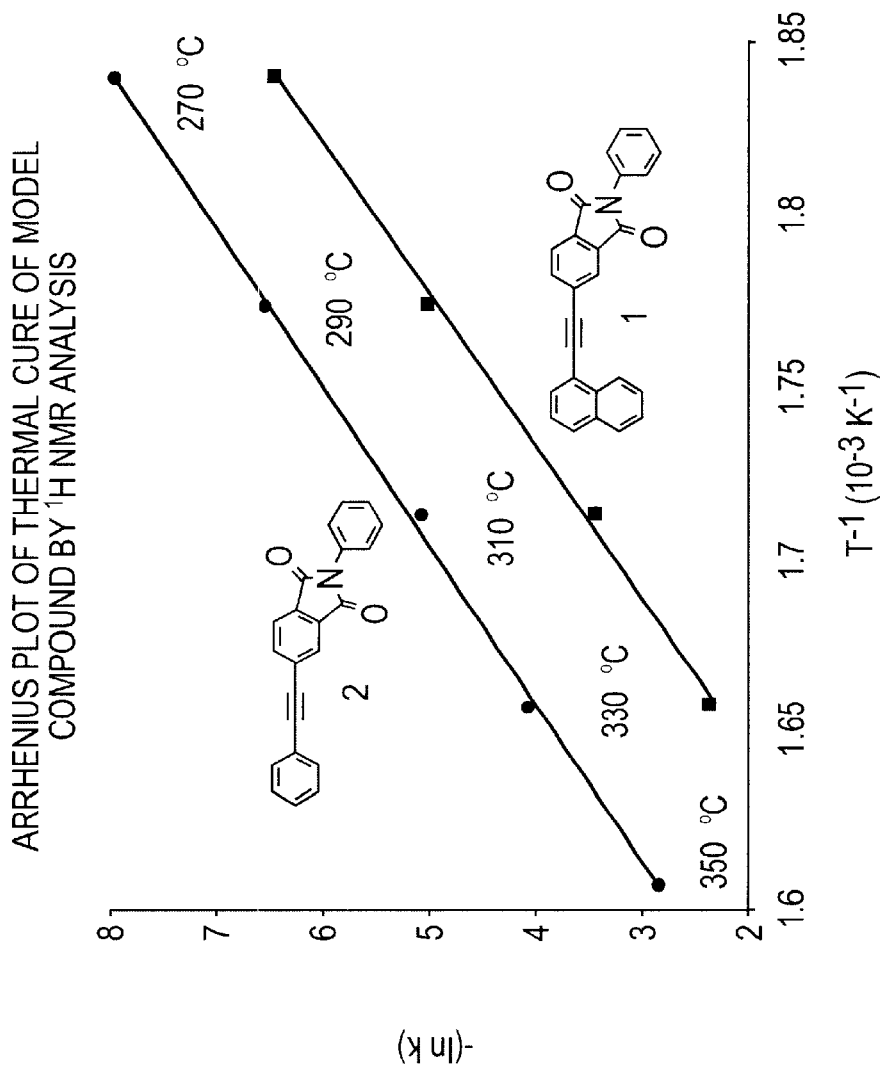
FIG. 7 is an Arrhenius plot of thermal cure kinetics of model compounds 1 (■) and 2 (♦). Regression data and calculated Arrhenius parameters are provided in Table 1.
Figure 8:
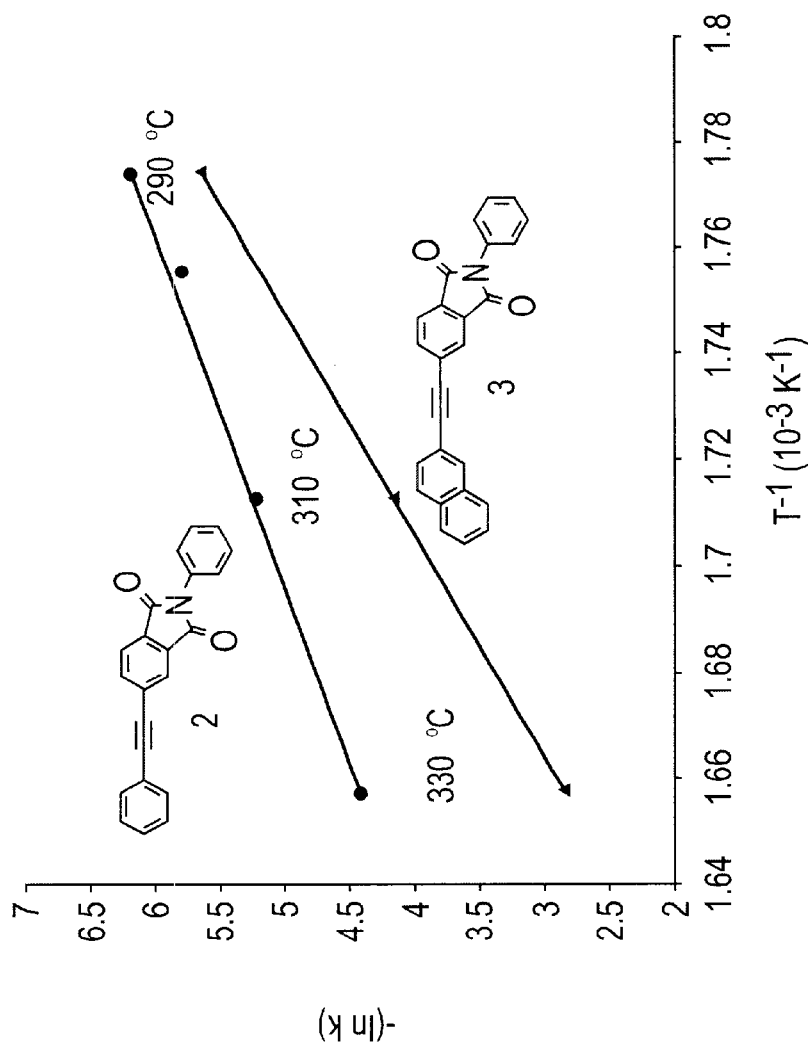
FIG. 8 is an Arrhenius plot of thermal cure kinetics of model compounds 2 (♦) and 3 (▲). Regression data and calculated Arrhenius parameters are provided in Table 1.
Figure 9:
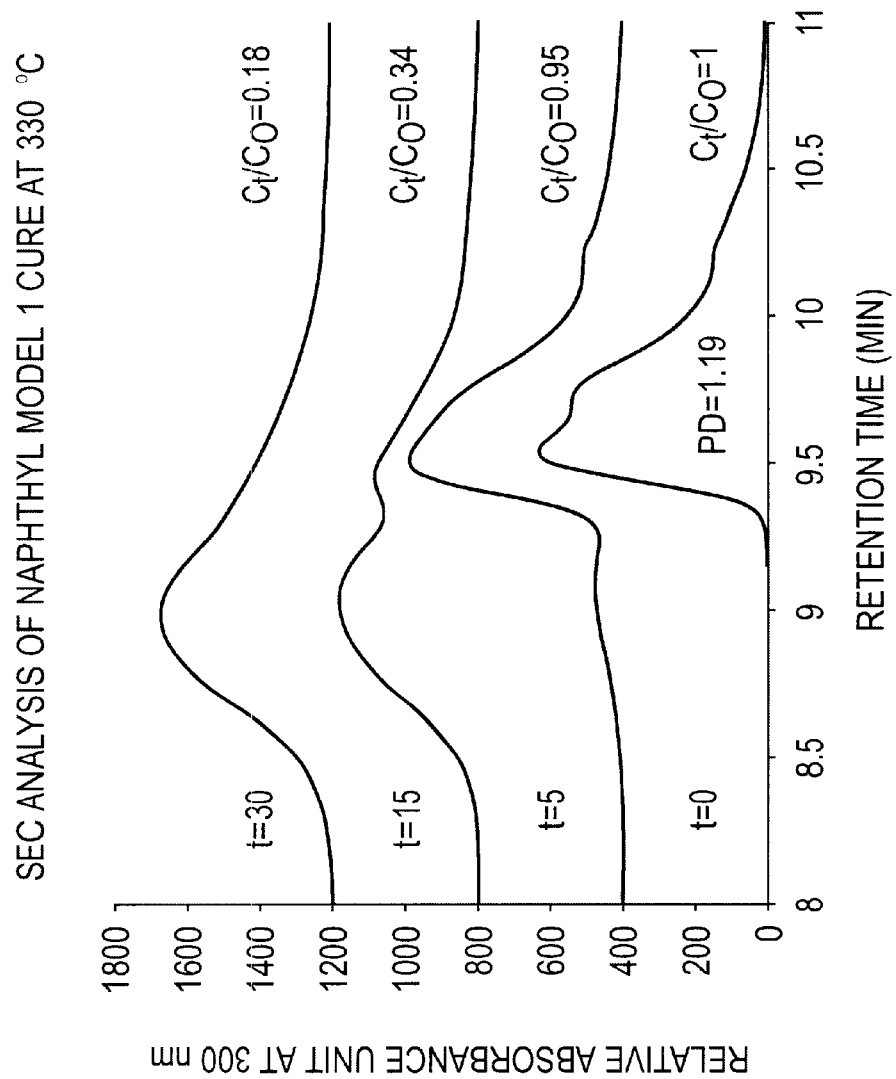
FIG. 9 shows SEC traces of cured model compound 1 at 330° C. Reaction time, reaction extent ($C_1/C_0$), and polydispersity (PD) of uncured 1 are indicated.

Analyses of the Kinetic Data for the Thermal Curing Reaction. Analysis of the thermal cure of model compounds 1 and 2 by $^1$H NMR and FT-IR spectroscopy followed by Arrhenius parameter evaluation revealed statistically indistinguishable energies of activation ($E_a$). The Arrhenius plots from $^1$H NMR and FT-IR spectroscopy are shown in FIGS. 7 and 8, respectively. However, the 1-naphthyl-ethynyl model compound (1) was found to cure significantly faster then the phenyl-ethynyl model compound (2) at any temperature studied. The difference in rates can be attributed to the pre-exponential factor (A), which accounts for stereo-electronic effects, collisional parameters, etc. Unfortunately, the interpretation of A is difficult and the extrapolation error is large. In terms of the thermodynamic parameters determined by Eyring analysis of the kinetic data, the difference in rates can be attributed to different activation entropies ($\Delta S_{act}$) of 1 and 2, whereas the activation enthalpies ($\Delta H_{act}$) are statistically indistinguishable. SEC analyses of several of the cured samples were found to correlate well with the calculated $C/C_0$ values as shown in FIG. 9. The nearly identical SEC traces of 1 and 2 are consistent with the formation of trimeric product with no higher molecular weight products detected even near the completion of the curing process (i.e. $C/C_0=0$). FT-IR analysis of the thermal cure kinetics of model compounds 2 and 3 via loss of the alkyne stretch peak revealed that the 2-naphthyl-ethynyl model (3) has a significantly higher $E_a/\Delta H_{act}$ than the phenyl-ethynyl model (2). 3 undergoes thermal curing at faster rates than 2, but slower than 1 at the temperatures studied. In addition, the $E_a/\Delta H_{act}$ of 2 as determined by FT-IR analysis is significantly lower than determined by $^1$H NMR analysis. Insolubility of 3 in common organic solvents prevented SEC analysis.

Figure 10:
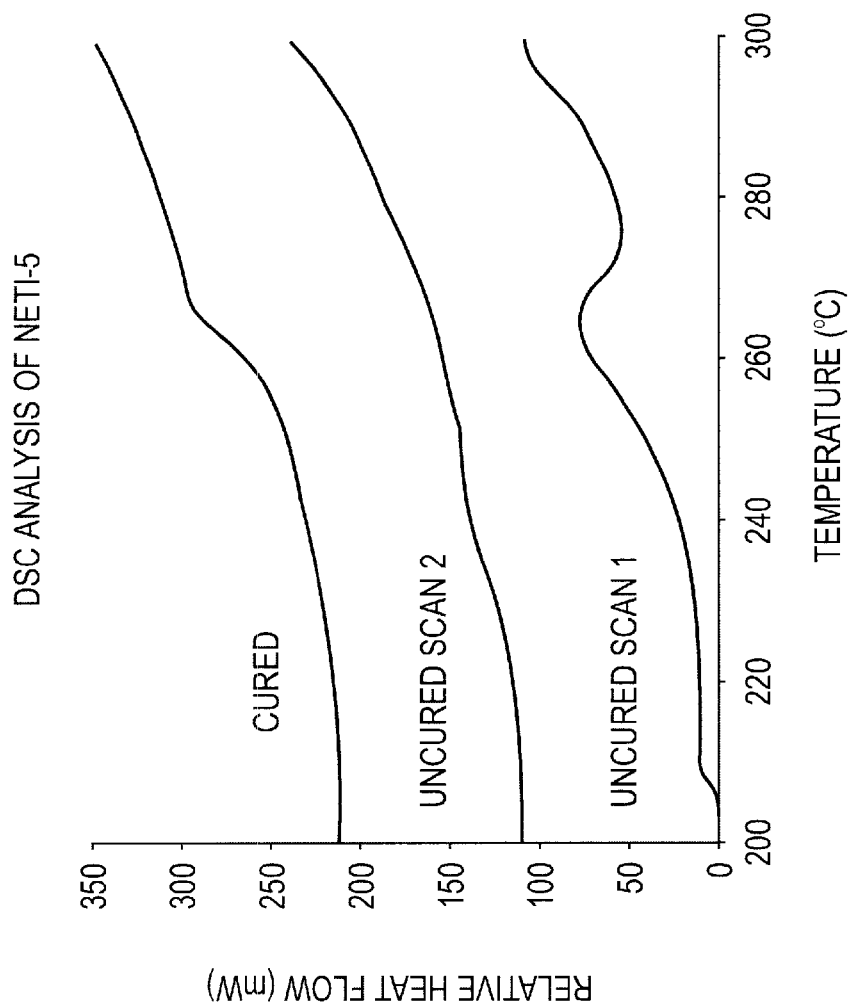
FIG. 10 shows a DSC traces of first and second scans of uncured NETI-5 and cured NETI-5 (1 h at 380° C.).
Figure 11:
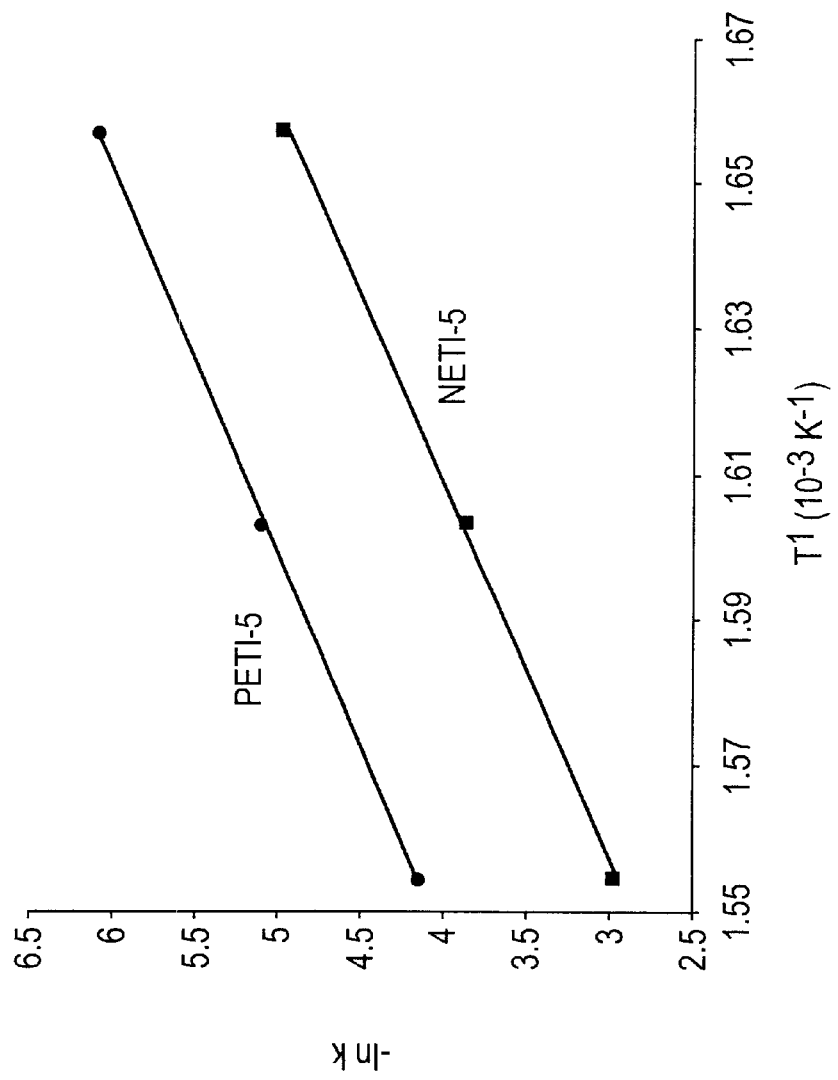
FIG. 11 shows an Arrhenius plot of thermal cure kinetics of NETI-5 (■) and PETI-5 (♦). Regression data and calculated Arrhenius parameters are provided in Table 1.

The DSC analysis of NETI-5 shown in FIG. 10 revealed a trend similar to that found in model compounds 1 and 2. The $E_a/\Delta H_{act}$ values of the oligomers were statistically indistinguishable, but the thermal cure rate of NETI-5 was found to be approximately three times faster than PETI-5 at all temperatures studied as shown in FIG. 11. Thus, NETI-5 can be cured at the same rate as PETI-5 but at approximately a 30° C. lower cure temperature. It is important to mention that in the literature cure rates for PETI-5 appear faster than measured and reported in our study. We believe this shows the importance of testing a standard, like PETI-5, to "calibrate" the reactivity of the new end-capping group. The very slight reduction in rate acceleration for the oligomer when compared to the model compound may be due to lower concentration of end-caps in the oligomers when compared to neat in 1 and 2 and/or the reduced mobility of the reactive group on the fairly rigid imide backbone. The model compounds accelerated curing reaction appears to translate to the oligomeric system. Table III shows the observed rates of thermal cure for the model compounds and oligomers at all temperatures studied.

TABLE III

Observed rates of thermal cure for model compounds and oligomers at all temperatures studied.

| Analysis Method | Sample | 270° C. | 290° C. | 310° C. | 330° C. | 350° C. | 370° C. |
|---|---|---|---|---|---|---|---|
| $^1$H NMR | 1 | $1.57_{10}^{-3}$ | $6.53_{10}^{-3}$ | $3.18_{10}^{-2}$ | $9.26_{10}^{-2}$ | | |
| $^1$H NMR | 2 | $3.53_{10}^{-4}$ | $1.43_{10}^{-3}$ | $6.09_{10}^{-3}$ | $1.68_{10}^{-2}$ | $5.71_{10}^{-2}$ | |
| FTIR | 2 | | $2.01_{10}^{-3}$ | $5.33_{10}^{-3}$ | $1.20_{10}^{-2}$ | | |
| FTIR | 3 | | $3.48_{10}^{-3}$ | $1.55_{10}^{-3}$ | $5.79_{10}^{-2}$ | | |
| DSC | NETI-5 | | | | $6.78_{10}^{-3}$ | $2.12_{10}^{-2}$ | $5.09_{10}^{-2}$ |
| DSC | PETI-5 | | | | $2.27_{10}^{-3}$ | $5.99_{10}^{-3}$ | $1.58_{10}^{-2}$ |

We demonstrated by $^1$H NMR spectroscopy that the 1-naphthyl-ethynyl imide model compound 1 cures significantly faster than the phenyl analog. In addition the 2-naphthyl-ethynyl imide (3) model compound also, cures faster than the phenyl, but not as fast as compound 1. The rate acceleration of the 1-naphthyl-ethynyl model permits a similar cure rate but at a temperature nearly 30° C. lower. At this point in time it appears by $^1$H NMR spectroscopy and SEC analysis that the thermal curing reaction(s) of 1–3 lead to similar products (possibly trimers). Interestingly, the single-crystal molecular-structures for 1 and 2 show a distinct difference in packing arrangements. It could be this difference in intermolecular packing (i.e. attractions) that may account for the significant differences in curing rates we have measured for the different aryl-ethynyl compounds. It is also important to mention that the reaction rates measured for the thermal cure of 2 by two methods of spectroscopic analysis ($^1$H NMR and FTIR spectroscopy) afford significantly different, as are the calculated Arrhenius and Eyring parameters. These data show the importance of utilizing a reference compound, like 2, to help standardize new compounds and new ways of measuring cure processes.

A key aspect to this work was the demonstration that the rate acceleration observed in the thermal cure of the model compound is also observed in the double end-capped imide oligomers. The net result is that we have developed naphthyl-ethynyl terminated imide (NETI-5) oligomer which will cure at competitive rates; however, at a significantly lower temperature (~30° C.).

EXAMPLE 2

General Methods. All manipulations of compounds and solvents were carried out using standard Schlenk techniques.

Tetrahydrofuran (THF) and triethylamine were purified by distillation under nitrogen from standard drying agents. N-methylpyrrolidinone was dried over molecular seives prior to use. $^1$H and $^{13}$C NMR measurements were performed using a Varian Oxford 300 MHz instrument. NMR chemical shifts are reported versus Me$_4$Si in $^1$H NMR spectra and assigning the CDCl$_3$ resonance at 77.00 ppm in $^{13}$C NMR spectra. The compounds 1-bromonaphthalene, 2-bromonaphthalene, 3,4'-oxydianiline and 3,3',4,4'-biphenyltetracarboxylic anhydride were purchased from Aldrich Chemical Co. The compound 1,3-bis(3-aminophenoxy)benzene was purchased from TCI America and trimethylsilylacetylene was purchased from GFS Chemicals, Inc. 4-Bromophthalic anhydride was supplied by NASA, Langley, Va. SEC analyses were performed by dilution in THF (2 mg/mL) and then injection onto a Hewlett-Packard 1100 HPLC (column: PL 300×7.5 mm, 5 µm particle size). Molecular weights are calculated relative to polystyrene standards. Elemental analyses were performed at Atlantic Microlab Inc., Norcross, Ga.

Synthesis of (N-phenyl)-4-(1-napthylethynyl) phthalimide. A flask charged with a 1:1 benzene/triethylamine mixture (30 ml), 4-(N-phenyl)-bromophthalimide (906 mg, 3.0 mmol), cuprous iodide (0.15 mmol, 30 mg), bis(triphenylphosphine)palladium dichloride (0.06 mmol, 40 mg) and triphenylphosphine (0.30 mmol, 80 mg) was treated with 1-naphthylacetylene (3.90 mmol, 600 mg) and heated at reflux for 3 h. The mixture was then cooled and filtered. The solid product was stirred in water (100 mL), filtered, and washed with water (3×10 mL). The crude product was recrystallized from toluene and vacuum dried at 85° C. to yield a yellow solid (560 mg, 50.0%): mp 176–178° C.; $^1$H NMR (CDCl$_3$, 300 MHz) δ7.40–7.68 (m, 8H), 7.83 (d, J=7.2 Hz, 1H), 7.91 (dd, J=6.5, 4.7 Hz, 1H), 7.98 (d, J=7.8 Hz, 1H), 8.03 (d, J=7.5 Hz, 1H), 8.20 (s, 1H), 8.42 Hz, 1H); $^{13}$C NMR (CDCl$_3$, 300 MHz) δ92.7, 92.9, 119.8, 124.0, 125.5, 126.1, 126.69, 126.72, 126.9, 127.4, 128.4, 128.7, 129.4, 130.1, 130.2, 130.5, 131.3, 131.8, 132.2, 133.32, 133.35, 137.3, 166.8. Anal. Calcd for C$_{26}$H$_{15}$NO$_2$: C, 83.63;H, 4.05. Found: C, 83.67;H, 4.12.

Synthesis of 4-(1-Naphthylethynyl)phthalic anhydride (4-NEPA). 4-NEPA was prepared according to the following scheme.

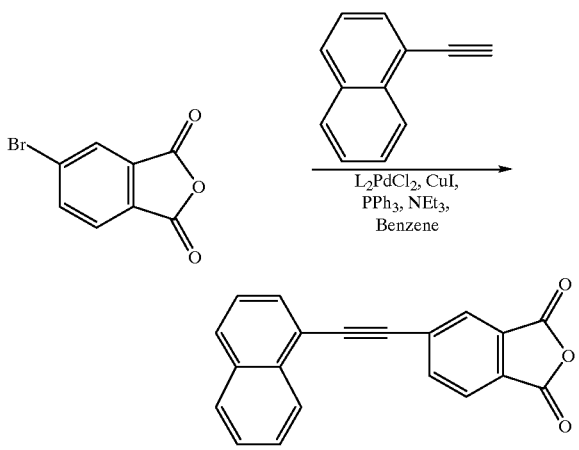

To a solution of 4-bromophthalic anhydride (4.54 g, 20.0 mmol), triphenylphosphine (520 mg, 2.0 mmol), cuprous iodide (190 mg, 1.0 mmol), bis(triphenylphosphine) palladium dichloride (280 mg, 0.4 mmol) in 2:1 triethylamine/benzene (75 mL) was added 1-ethynylnaphthalene (4.94 g, 32.5 mmol) in benzene (25 mL) by cannula transfer and the mixture was heated at reflux for 2 h. The cooled solution was filtered and the precipitate was added to water (150 mL), filtered and washed with water (3×5 mL). The crude yellow solid was recrystallized from toluene, filtered and washed with hexanes (3×5 mL). The product was then added to 0.15 M NaHCO$_{3(aq)}$, stirred vigorously for 1 h and filtered. The yellow solid was dried at reduced pressure to constant weight to yield 4-(1-naphthylethynyl)phthalic anhydride (2.16 g, 36.2%). mp 220–222° C.; $^1$H NMR (CDCl$_3$, 300 MHz) δ7.48–7.68 (m, 3H), 7.82 (d, J=7.2 Hz, 1H), δ7.92 (t, J=8.1 Hz, 2H), δ7.99 (d, J=7.8 Hz, 1H), δ8.07 (d, J=8.0 Hz, 1H), δ8.20 (s, 1H), δ8.35 (d, J8.1 Hz, 1H); $^{13}$C NMR (CDCl$_3$, 300 MHz) δ92.0, 94.6, 119.3, 125.5, 125.8, 125.9, 127.0, 127.6, 128.4, 128.8, 129.7, 130.6, 131.7, 131.9, 132.2, 133.3, 133.4, 138.7, 162.3, 162.3. Anal. Calcd for C$_{20}$H$_{10}$O$_3$: C, 80.53;H, 3.38. Found: C, 80.37;H, 3.36.

General X-ray Crystallographic Procedures. Crystalline samples of 1 and 2 were inspected by microscopy and were examined a CAD4 diffractometer equipped with graphite-monochromated Mo Kα radiation (λ=0.71073 Å). Details of the data collection and refinement are included in Table E (supplemental material).

X-ray Structure Determination for N-phenyl4-(1-naphthylethynyl)phthalimide (1). An irregular shaped yellow specimen of approximate dimensions 0.41×0.38×0.20 was cut from a larger block and was mounted with Infinium Parabar 10312 oil at low temperature on a quartz fiber. The crystal was judged to be of acceptable quality by the collection of several ω scans whose average width at half height was 0.288°. The orthorhombic symmetry was confirmed by axial photography. Three periodically monitored intensity check reflections displayed no decay of intensity throughout data collection. An empirical absorption correction was applied to the data. The data were actually collected for monoclinic symmetry, but the redundant data were averaged prior to final refinement. The structure was solved by using the teXsan software package. Although attempts to solve in the centric space group, Pbcm (57). were unsuccessful and SHELX 97 produced poor FOM's, all of the non-hydrogen atoms of the three molecules in the asymmetric unit were revealed by the application of SHELX 97 in the a centric space group, Pca21(29). The rapid fall-off of diffraction intensity at high angle coupled with the need to refine three molecules in the unit cell produced an unfortunately small data-to-parameter ratio of 5.4:1, in spite of refining the non-hydrogen atoms isotropically rather than anisotropically. Hydrogen atoms were included in calculated positions. The twist of each of the molecules and lack of any correlation coefficients greater than 0.5 in the final least squares cycle was further evidence that a centric space group was the correct choice. The maximum residual electron density was 0.27 e-/Å$^3$ in the final difference map.

X-ray Structure Determination N-phenyl-4-phenylethynylphthalimide (2). A colorless triangular plate measuring approximately 0.28×0.30×0.33 mm was mounted with epoxy on the end of a quartz fiber. The quality of the crystal was established by five scans whose average width at half height were less than 0.3000, and the monoclinic symmetry was confirmed by axial photographs. Three periodically monitored intensity check reflections indicated a decay of only 0.5% throughout the course of data collection so a decay correction was not applied to the data. As with the previous structure, there was some difficulty establishing the correct space group. Attempts to solve the data in P2/a (#13, cell choice #3) or P21/a (#14) produced only the phthalimide moiety plus an incomplete phenyl ring off the nitrogen with R factors above 0.3. Application of the SHELX 97 solution program in the space group, Pa (#7, cell choice #3), revealed all of the non-hydrogen atoms in the structure with R factors under 0.1 even for the first least squares refinement. Analysis of the packing diagram verified the a centric symmetry of the unit cell (vide supra). All non-Hydrogen atoms were refined isotropically; Hydrogen atoms were included in calculated positions. The final difference map displayed a maximum residual electron density of 0.28 e−/Å$^3$.

Synthesis of Naphthyl-Ethynyl Terminated Imide oligomer (NETI-5). The NETI-5 oligomer was prepared according to the following scheme.

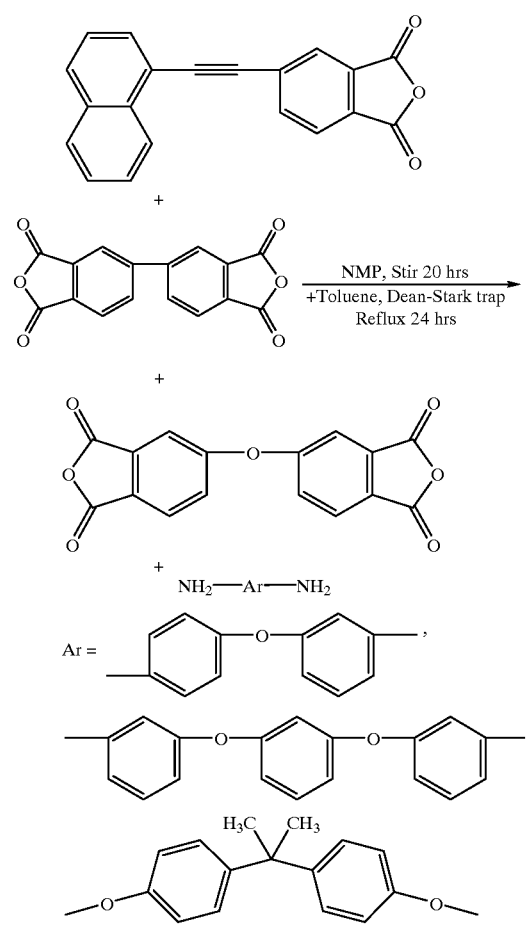

To a solution of 1,3-bis(3-aminophenoxy)benzene (0.15 equiv, 0.19 g, 0.66 mmol) and 3,4'-oxydianiline (0.85 equiv, 0.75 g, 3.8 mmol) in N-methylpyrrolidinone (35 mL) at 0 °C. was added 3,3',4,4'-biphenyltetracarboxylic dianhydride (0.91 equiv, 1.18 g, 4.02 mmol) and 4-(1-naphthylethynyl)phthalic anhydride (0.18 equiv, 0.24 g, 0.79 mmol). The solution was warmed to 25° C. and stirred under a nitrogen atmosphere for 20 h. The flask was equipped with a Dean-Stark trap and condenser, toluene was added (100 mL), and the mixture was heated at reflux for approximately 20 h. The cooled solution was filtered and the precipitate added to water (150 mL), filtered and washed successively with warm water (3×10 mL) and methanol (3×10 mL). The powders were then dried at 85° C. and reduced pressure to constant weight to yield NETI-5 (2.82 g, 96.6%): $M_w$=2907 g/mol; PD=1.66.

Synthesis of 4-(9-anthracenylethynyl)phthalic anhydride. The anthracenyl compound was prepared according to the following scheme:

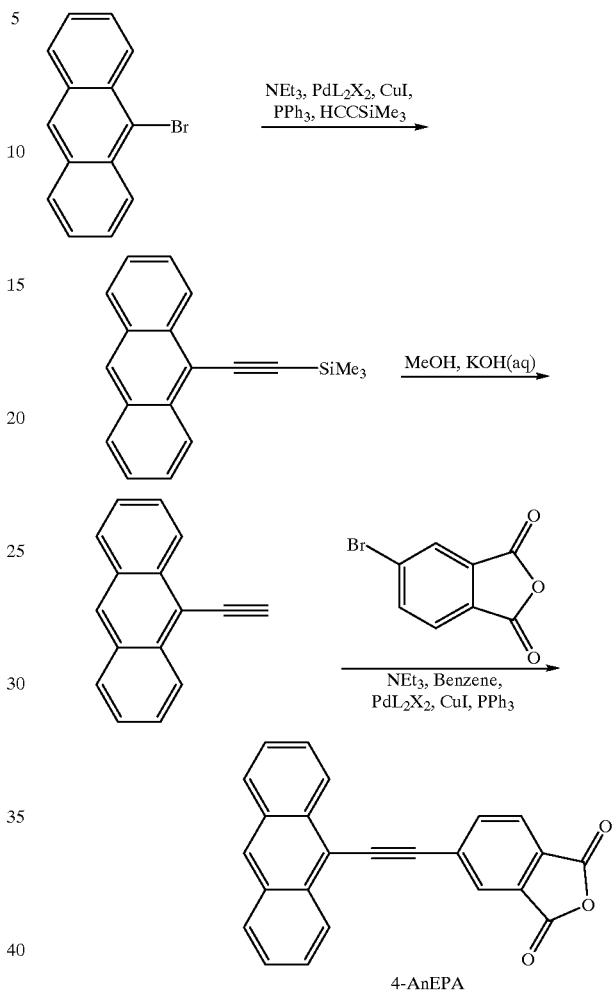

To a solution of 9-bromoanthracene (1.35 g, 5.25 mmol), triphenylphosphine (138 mg, 0.53 mmol), copper iodide (50 mg, 0.26 mmol), and bis(triphenylphosphine)palladium dichloride (74 mg, 0.11 mmol) in 1:1 triethylamine/benzene (35 mL) was added trimethylsilylacetylene (1.11 mL, 7.85 mmol) and the solution was heated at reflux 1 h. The cooled solution was diluted with ethyl ether (100 mL) and filtered. The organic was washed with $H_2O$ (3×100 mL), dried over $Na_2SO_4$, and filtered. Solvents were removed under reduced pressure to yield crude 9-anthracenyltrimethylsilylacetylene. The crude oil was dissolved in methanol (150 mL) and 3.5 M KOH$_{(aq)}$ (2 mL) was added and stirred 1 h. The reaction was quenched with $H_2O$ (150 mL) and the product was extracted with hexane (3×100 mL). The combined organic layers were dried over $Na_2SO_4$, filtered, and solvents were removed under reduced pressure to yield crude 9-anthracenylacetylene. The crude oil was dissolved in benzene (10 mL) and added to a solution of 4-bromophthalic anhydride (0.908 g, 4.0 mmol), triphenylphosphine (105 mg, 0.40 mmol), copper iodide (39 mg, 0.20 mmol), and bis(triphenylphosphine)palladium dichloride (56 mg, 0.08 mmol) in 2:1 triethylamine/benzene (30 mL) by cannula transfer and heated at reflux 1 h. The cooled solution was filtered and the precipitate was diluted with 0.5 M NaHCO$_3$(aq) (100 mL) and stirred vigorously 1 h. The mixture was diluted with acetone (50 mL) and filtered. The crude product was recrystallized from toluene and dried under reduced pressure to yield 4-(9-anthracenylethynyl) phthalic anhydride (1.03 g, 73.8%) as a deep red solid. $^1$H NMR (DMSO-d$_6$, 300 MHz) δ7.77 (t, J=7.1 Hz, 2H), 7.88 (t, J=7.2 Hz, 2H), 8.29–8.34 (m, 3H), 8.56 (d, 7.8 Hz, 1H), 8.75 (s, 1H), 8.83 (d, J=8.7 Hz, 2H), 8.92 (s, 1H).

It will be readily understood by those persons skilled in the art that the present invention is susceptible to broad utility and application. Many embodiments and adaptations of the present invention other than those herein described, as well as many variations, modifications and equivalent arrangement, will be apparent from or reasonably suggested by the present invention and the foregoing description without departing from the substance or scope of the present invention.

Accordingly, while the present invention has been described in detail in relation to its preferred embodiment, it is to be understood that this disclosure is only illustrative and exemplary of the present invention and is made merely for purposes of providing a full and enabling disclosure of the invention. The foregoing disclosure is not intended to be construed to limit the present invention or otherwise exclude any other embodiments, adaptations, variations, modifications or equivalent arrangements, the present invention being limited only by the claims and the equivalents thereof.

What is claimed is:

1. A compound having the formula:

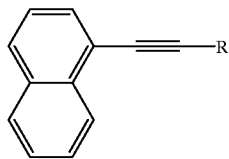

wherein R is selected from the group consisting of polymers, oligimers and reactive moieties.

2. The compound of claim 1 wherein R is a polymer selected from the group consisting of polyimides, polysulfones, polyaromatics, and polyolefins.

3. The compound of claim 1 wherein R is a reactive moiety selected from the group consisting of phthalimide and phthalic anhydride.

4. A method for making an naphthyl-ethynyl capped compound comprising:
reacting the a naphthyl-ethynyl compound having the formula:

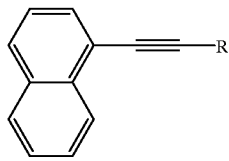

with a reactive compound wherein R is an anhydride moiety to produce a naphthyl-ethynyl capped compound.

5. The method of claim 4 wherein the reactive compound is selected from the group consisting of amines, diamines, triamines, compounds having more than three amino functional groups, phenoxy benzyl diamines, diamines containing aryl substituents, sulfonyl containing compounds, halide containing compounds, ester containing compounds, amide containing compounds, and combinations thereof.

6. The method of claim 4 wherein the reactive compound is a thermally stable aromatic bis(amine).

7. The method of claim 4 wherein the reactive compound is selected from the group consisting of

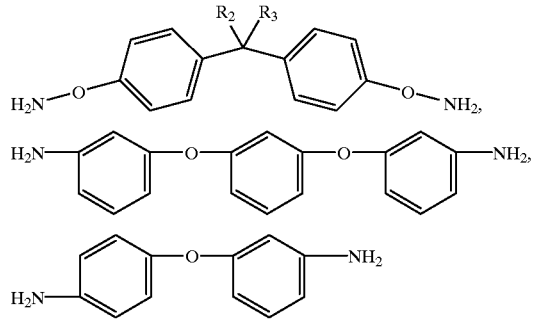

and combination thereof, wherein R$_2$ and R$_3$ are alkyl moieties.

8. The method of claim 7 wherein R$_2$ and R$_3$ are methyl.

9. The method of claim 4 wherein the anhydride is selected from the group consisting of 3,3',4,4'-biphenyltetracarboxylic dianhydride, 4,4'-oxydiphthalic anhydride, and combinations thereof.

10. The method of claim 4 wherein R is phthalic anhydride.

11. A method for making a polymer comprising:
reacting

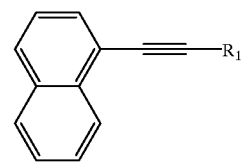

with

X—R$_2$ to produce

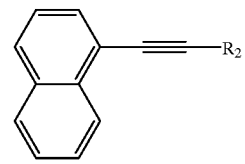

wherein R$_1$ is a metal anion, X is a halogen, and R$_2$ is a polymer.

12. A compound having the formula:

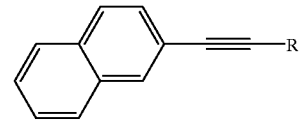

wherein R is selected from the group consisting of polymers, oligimers and reactive moieties.

13. The compound of claim 12 wherein R is a polymer selected from the group consisting of polyimides, polysulfones, polyaromatics, and polyolefins.

14. The compound of claim 12 wherein R is a reactive moiety selected from the group consisting of phthalimide and phthalic anhydride.

15. A method for making an naphthyl-ethynyl capped compound comprising:

reacting the a naphthyl-ethynyl compound having the formula:

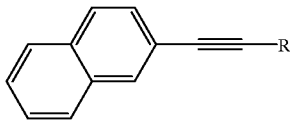

with a reactive compound wherein R is an anhydride moiety to produce a naphthyl-ethynyl capped compound.

16. The method of claim 15 wherein the reactive compound is selected from the group consisting of amines, diamines, triamines, compounds having more than three amino functional groups, phenoxy benzyl diamines, diamines containing aryl substituents, sulfonyl containing compounds, halide containing compounds, ester containing compounds, amide containing compounds, and combinations thereof.

17. The method of claim 15 wherein the reactive compound is a thermally stable aromatic bis(amine).

18. The method of claim 15 wherein the reactive compound is selected from the group consisting of

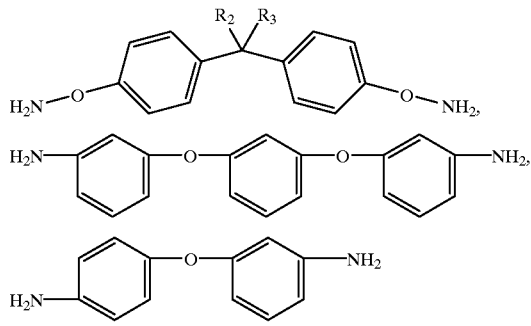

and combinations thereof, wherein $R_2$ and $R_3$ are alkyl moieties.

19. The method of claim 18 wherein $R_2$ and $R_3$ are methyl.

20. The method of claim 15 wherein the anhydride is selected from the group consisting of 3,3',4,4'-biphenyltetracarboxylic dianhydride, 4,4'-oxydiphthalic anhydride, and combinations thereof.

21. The method of claim 15 wherein R is phthalic anhydride.

22. A method for making a polymer comprising:

reacting

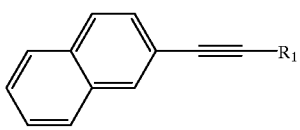

with $X-R_2$ to produce

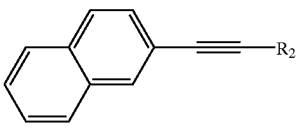

wherein $R_1$ is a metal anion, X is a halogen, and $R_2$ is a polymer.

23. A compound having the formula:

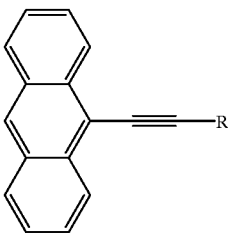

wherein R is selected from the group consisting of polymers, oligimers and reactive moieties.

24. The compound of claim 23 wherein R is a polymer selected from the group consisting of polyimides, polysulfones, polyaromatics, and polyolefins.

25. The compound of claim 23 wherein R is a reactive moiety selected from the group consisting of phthalimide and phthalic anhydride.

26. A method for making a anthracenyl-ethynyl capped compound comprising:

reacting the a anthracenyl-ethynyl compound having the formula:

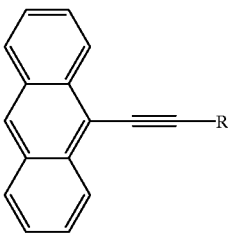

with a reactive compound wherein R is an anhydride moiety to produce a anthracenyl-ethynyl capped compound.

27. The method of claim 26 wherein the reactive compound is selected from the group consisting of amines, diamines, triamines, compounds having more than three amino functional groups, phenoxy benzyl diamines, diamines containing aryl substituents, sulfonyl containing compounds, halide containing compounds, ester containing compounds, amide containing compounds, and combinations thereof.

28. The method of claim 26 wherein the reactive compound is a thermally stable aromatic bis(amine).

29. The method of claim 26 wherein the reactive compound is selected from the group consisting of

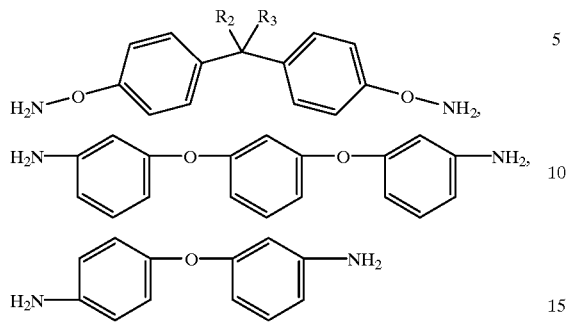

and combinations thereof, wherein $R_2$ and $R_3$ are alkyl moieties.

30. The method of claim 29 wherein $R_2$ and $R_3$ are methyl.

31. The method of claim 26 wherein the anhydride is selected from the group consisting of 3,3',4,4'-biphenyltetracarboxylic dianhydride, 4,4'-oxydiphthalic anhydride, and combinations thereof.

32. The method of claim 26 wherein R is phthalic anhydride.

33. A method for making a polymer comprising:
reacting

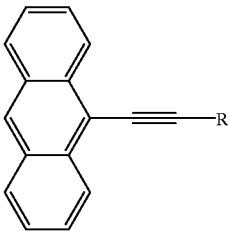

with

to produce

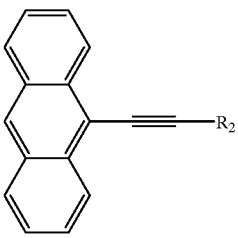

wherein $R_1$ is a metal anion, X is a halogen, and $R_2$ is a polymer.

* * * * *